US010603490B2

(12) United States Patent
Gifford, III et al.

(10) Patent No.: US 10,603,490 B2
(45) Date of Patent: Mar. 31, 2020

(54) TEMPORARILY IMPLANTABLE GI SENSOR AND STIMULATOR AND RELATED METHODS

(71) Applicant: The Foundry, LLC, Menlo Park, CA (US)

(72) Inventors: Hanson S. Gifford, III, Woodside, CA (US); Mark Deem, Mountain View, CA (US)

(73) Assignee: The Foundry LLC, Menlo Park, CA (US)

(*) Notice: Subject to any disclaimer, the term of this patent is extended or adjusted under 35 U.S.C. 154(b) by 33 days.

(21) Appl. No.: 15/521,439

(22) PCT Filed: Oct. 23, 2015

(86) PCT No.: PCT/US2015/057248
§ 371 (c)(1),
(2) Date: Apr. 24, 2017

(87) PCT Pub. No.: WO2016/065342
PCT Pub. Date: Apr. 28, 2016

(65) Prior Publication Data
US 2017/0361090 A1    Dec. 21, 2017

Related U.S. Application Data

(60) Provisional application No. 62/067,784, filed on Oct. 23, 2014.

(51) Int. Cl.
*A61N 1/36* (2006.01)
*A61N 1/05* (2006.01)

(52) U.S. Cl.
CPC ....... *A61N 1/36007* (2013.01); *A61N 1/0507* (2013.01)

(58) Field of Classification Search
CPC .......................... A61N 1/36007; A61N 1/0507
See application file for complete search history.

(56) References Cited

U.S. PATENT DOCUMENTS 3,411,507 A    11/1968  Wingrove
6,754,536 B2 *  6/2004  Swoyer ............. A61B 5/04884
                                                      607/40
(Continued)

OTHER PUBLICATIONS

Bilgutay, Aydin M. et al., "Gastro-Intestinal Pacing: A New Concept in the Treatment of Ileus", Annals of Surgery, vol. 153, No. 3, Sep. 1963; pp. 338-347.

(Continued)

*Primary Examiner* — Amanda K Hulbert
*Assistant Examiner* — Natasha Patel
(74) *Attorney, Agent, or Firm* — Downs Rachlin Martin PLLC

(57) ABSTRACT

GI tract treatment and monitoring devices configured for temporary implantation in the GI tract and non-invasive removal via natural body processes are disclosed. Methods of implantation, treatment and monitoring with disclosed devices are also disclosed. Devices include bio-active fixation that allows removal from the body by natural processes after a time that may be engineered in the fixation elements. In some embodiments, devices are configured to be implanted on GI tract tissue and transmurally migrate into the GI tract to be passed from the body. In other embodiments, devices are configured for placement within the GI tract via a delivery tube such as an NJ/NG tube. Embodiments include stimulation devices for treating conditions such as ileus and sensors for monitoring GI leaks and/or biological or chemical markers for various GI tract conditions.

19 Claims, 11 Drawing Sheets

(56) References Cited

U.S. PATENT DOCUMENTS

| | | |
|---|---|---|
| 2004/0093039 A1 | 5/2004 | Schumert |
| 2005/0222537 A1 | 10/2005 | Dinsmoor et al. |
| 2006/0247720 A1* | 11/2006 | Starkebaum ......... A61B 5/6882 |
| | | 607/40 |
| 2006/0265021 A1 | 11/2006 | Herbert et al. |
| 2008/0065168 A1* | 3/2008 | Bitton ................ A61N 1/36007 |
| | | 607/40 |
| 2011/0125211 A1 | 5/2011 | Griffin et al. |
| 2012/0116528 A1* | 5/2012 | Nguyen ................... A61F 2/04 |
| | | 623/23.7 |

OTHER PUBLICATIONS

Chen et al., "Gastric pacing improves emptying and symptoms in patients with gastroparesis" Gastroenterology, Mar. 1998; 114(3): 456-61.

International Search Report and Written Opinion dated Mar. 3, 2016, in connection with PCT/US15/57248, filed Oct. 23, 2015.

* cited by examiner

TEMPORARILY IMPLANTABLE GI SENSOR AND STIMULATOR AND RELATED METHODS

FIELD

Embodiments of the present invention relate to sensors and stimulators implantable on or in the gastrointestinal tract, and, more particularly temporarily implantable gastrointestinal sensors and stimulators and related methods.

BACKGROUND

Gastroparesis and ileus are adverse medical conditions in which normal gastric motor function and/or intestinal peristalsis are impaired. Patients with these conditions typically experience symptoms of nausea or vomiting, and gastric discomfort such as bloating. This can cause reduced food intake and reduced caloric absorption by the intestinal system, which may adversely affect patient health. These conditions are often seen in patients after abdominal surgery or in patients in the intensive care unit. The delayed return to normal gastrointestinal function can result in many days of extra hospitalization, and cause significant complications for patients due to a lack of caloric absorption.

Pacing type stimulation has been proposed to restart peristalsis in post-surgical patients suffering from ileus. For example, U.S. Pat. No. 3,411,507, entitled "Method of Gastrointestinal Stimulation With Electrical Pulses," describes a transoral system for gastrointestinal (GI) tract pacing to treat ileus. Chen et al., "Gastric pacing improves emptying and symptoms in patients with gastroparesis," Gastroenterology, 1998 March; 114(3):456-61, also describe pacing to treat ileus. Devices are also available from a number of manufacturers designed to, for example, electrically pace the stomach or GI tract to treat obesity. Such pacing devices are similar in form and function to cardiac pacemakers, and typically consist of a permanently or long-term implanted stimulator and contact leads. A variety of other surgically implanted stimulators have been made and tested to treat other conditions such as gastrointestinal paresis.

In addition to stimulation, there are many situations in which it may be desirable to monitor conditions within, or stimulate or manipulate tissue of the GI tract. For example, devices such as pill-shape cameras are placed into the GI tract by swallowing and allowed to pass through via natural peristaltic transport and excretion. Other devices allowed to pass through the GI tract include certain anastomosis devices used to join the ends of the GI tract together after resection surgery. After sufficient time, the devices fragment or fall apart after portions of them dissolve, and the resulting fragments pass.

However, many known devices or solutions to gastric stimulation or sensing have various drawbacks related to invasive placement or removal, or for existing temporary devices, awkward delivery and a limited time of treatment.

It is known from the surgical literature that non-resorbable foreign matter which is left in contact with the outer wall (serosa) of the stomach or gastrointestinal tract can become integrated into the wall of the GI tract. Over the course of days to weeks, it can actually migrate partially or completely through the wall of the GI tract. Suture, peri-strips, hernia mesh, and silicone bands have all been reported in the clinical literature as having undergone transmural migration.

Transmural device migration can become a significant complication when it happens unexpectedly, such as has occurred with some gastric surgery devices. These incidents often require surgical or laparoscopic or endoscopic interventions. Partial migrations through the wall almost always require surgical intervention. In some cases, however, the materials or devices migrate completely into the GI tract, and are removed endoscopically. It is unknown how often and whether complete device migrations go undetected and simply pass through the GI tract and out of the body.

SUMMARY OF THE DISCLOSURE

Embodiments disclosed herein include methods and devices employing intentional transmural transmigration of the devices from the outside of the GI tract to the inside. In described embodiments, sensors, stimulators or other devices are temporarily placed at a site of interest within the abdomen, but where it may be undesirable to reenter the body to remove the device. Thus, in aspects of the present disclosure, devices are designed and materials selected so that the sensors, stimulators or other devices pass naturally from the GI tract. In some embodiments, devices may be initially placed within the GI tract and secured to an internal wall structure by a bio-erodible fixation means. In other embodiments, devices may initially reside on the outside of the GI tract while operation is desired, but which will migrate transmurally into the lumen of the GI tract thereafter.

In one implementation, the present disclosure is directed to a temporary implantable GI device. The device includes housing securable to a tissue structure of the GI tract; interface elements disposed with the housing to monitor or stimulate the GI tract through the housing; functional elements within the housing configured to provide power and control for the interface elements; one or more bio-active fixation elements configured to secure the housing at a selected treatment location on or in the GI tract structure and to release the housing into the GI tract after a determined time so as to be passed from the body through natural processes of the GI tract after the release.

In another implementation, the present disclosure is directed to a method for stimulating or monitoring in the GI tract. The method includes selecting a target location on or in a GI tract structure; delivering a treatment or monitoring device to the target location, the device comprising at least one bio-active fixation element; securing the device at the target location with the bio-active fixation element; transforming the bio-active fixation element so as to release the device from the target location into a lumen of the GI tract; operating the device within the lumen to treat or monitor the GI tract for a predetermined time; and allowing the device to be passed out of the body through the GI tract after the predetermined time.

In still another implementation, the present disclosure is directed to a method of diagnosis or treatment in the GI tract by temporary implantation and non-invasive removal of a diagnostic or treatment device. The method includes securing the device at a selected location on or in GI tract tissue with a bio-active fixation element specifically configured to release the device into the GI tract after a determined time so as to be passed from the body through natural processes of the GI tract after the release; and operating the device before the end of the determined time.

In yet another implementation, the present disclosure is directed to a temporary GI treatment or monitoring device allowing non-invasive removal. The treatment or devices includes a sealed housing of bio inert material; a bio-active layer on at least a portion of the housing, the bio-active layer specifically configured to promote transmural migration of the device through GI tract tissue; fixation means on the housing; at least one interface element configured to provide treatment or to monitor and to extend through or beyond the housing; and control and power supply components disposed in the housing communicating with the at least one interface element.

In still yet another implementation, the present disclosure is directed to a device for temporary implantation in tissues of the GI tract. The devices includes a self-contained and self-powered stimulator or sensor, with pre-set operating parameters, specifically configured for transmural migration through GI tract tissue from an implantation location into the GI tract to be naturally passed from the body without surgical intervention after implantation.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DESCRIPTION OF EMBODIMENTS

Figure 1:
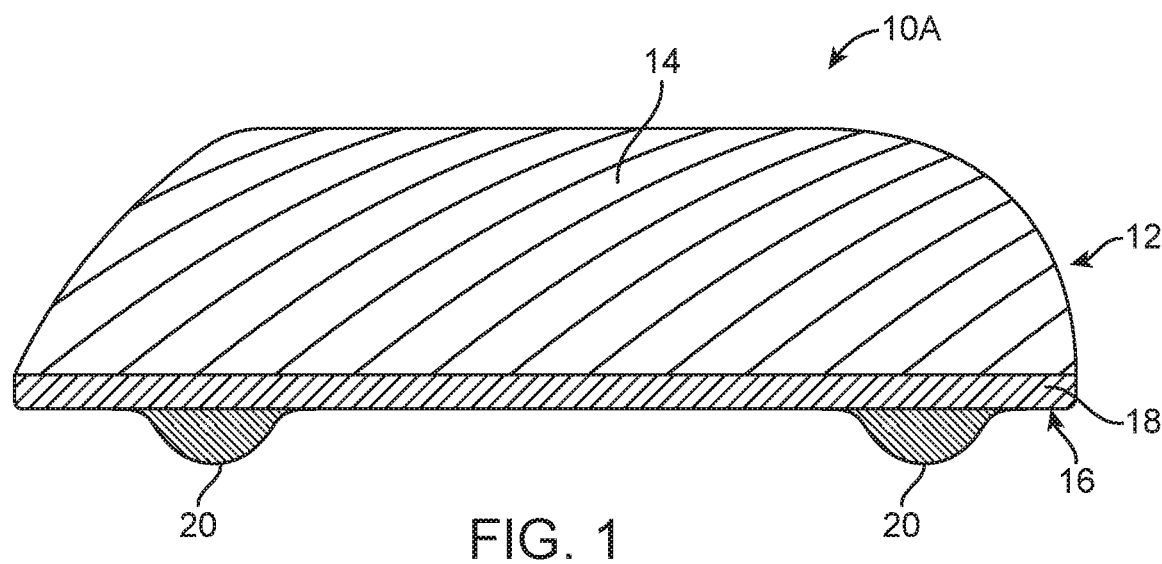
FIG. 1 schematically illustrates one exemplary embodiment of a stimulation device encapsulated in a coating or fabric to encourage tissue ingrowth and transmural migration.

Illustrative embodiments disclosed herein include temporarily implantable sensors and stimulators configured for placement on or in an outer surface or wall structure defining the GI tract of a patient, or within the GI tract itself. The terms "temporary implantation" or "temporarily implantable" as used herein with reference to embodiments of the disclosed devices and methods means to remain in the body temporarily, and then pass through the GI tract by natural processes without any action or intervention by the patient or doctor. Thus, disclosed devices are configured to remain at least substantially at the placement location during an active period of operation. However, when the desired active period is complete, the disclosed devices are configured to be removed through natural expulsion processes of the body via the GI tract. Various embodiments of bio-active fixation elements that transform to release the devices are employed to fix and then release devices as described herein.

In some embodiments, the removal mode involves transmural migration of the device from a placement location on or in the wall structure of the GI tract to the inside GI tract. Embodiments configured for transmural migration are generally self-contained in a sealed housing and of a size that fits within the intestinal tract without leads or physical electrical connections to a separate controller/power supply and unconnected to a catheter shaft, or other structures that extend to remote locations internally or externally. Such embodiments may also include smooth outer surface, materials that encourage migration, streamlined or pill-like shape without protrusions, or other surface discontinuities, that would hinder migration through tissue or excreting from the GI tract by natural processes. In other embodiments, devices are initially placed within the GI tract and secured to internal wall structures with bio-erodible fastening means configured to release the device after the treatment period. These embodiments may also comprise sealed housings that are streamlined or pill-like in shape, without protrusions or other surface discontinuities to hinder passage through the GI tract by natural processes. In each case, once free within the GI tract, the devices naturally pass from the body. Illustrative embodiments also include methods related to the placement and use of disclosed devices.

While a wide variety of permanently implantable internal and external stimulators and sensors are used for many medical applications, in some instances patients may require only temporary treatment. In such cases, conventionally implanted devices often require an additional, sometimes invasive procedure for both introduction and removal. For example, many patients require shorter term assistance in modifying their lifestyle in order to establish weight loss, and once more healthful habits are developed, may no longer require device assistance. Other indications where temporary treatment may be desirable include modulation of peristalsis of the GI tract, for example to treat ileus, or where stimulation or modulation of the nerves of the GI tract, either blocking or stimulating these nerves, may have beneficial effects. Specific treatment algorithms, whether for sensing or stimulating, may be readily devised by healthcare providers based on specific clinical indications and known algorithms and treatment protocols using devices and methods disclosed herein.

As illustrated in FIG. 1, an exemplary embodiment of a stimulation device 10A comprises a housing or case 12 substantially encapsulated in a coating or fabric 14 that encourages ingrowth of tissue into the device. Serosa-contacting side 16 may comprise a base layer 18 of a material configured to adhere to the serosa. Electrodes 20 extend through, or are disposed within gaps in the serosa-contacting base layer 18 to make electrical contact with and allow stimulation signals to reach the target tissue.

Housing or casing 12 may be formed of suitable biocompatible materials, typically a bio-inert material, that will maintain integrity over time to maintain isolation of internal device components, such as power source and control circuitry, from the surrounding environment. While casing 12 may maintain integrity, encapsulating coating or fabric 14 ensures that the device as a whole is compatible with the tissue into which it is to be absorbed and facilitates transmural migration through that tissue into the GI tract. Layer 14 thus forms a bio-active fixation element comprised of a material or surface treatment specifically configured for tissue ingrowth to permit transmural migration of the device through the tissue structure into the GI tract. In exemplary embodiments, layer 14 may comprise open weave fabrics, or approximately 80-120µ inter nodal distance (IND) expanded polytetrafluoroethylene (ePTFE). Other coatings or fabrics as described below also may be employed in or as layer 14.

As mentioned above, serosa contacting side 16 comprises a base or base layer 18, which may be made of or include a material configured to promote adhesion to the serosa. One example of such a material is Progrip™ mesh manufactured by Covidien, which is a woven mesh that creates a biological hook-and-loop-type self-adhesion with muscle. Modifying the chosen material specifically to attach to the serosa of the GI tract, for example by increasing its porosity or coating it with a slightly inflammatory material, such as poly-L-lactide (PLLA), could enable customized adhesion. Other fixation materials and techniques may be supplementarily or alternatively employed. For example, the device may be attached to the wall of the GI tract by any traditional surgical method such as suture, staple, rivet, bio-adhesives, cyanoacrylate adhesives or the like. Additional fixation means may be provided on the device for this purpose; for example, loops, fabric tabs, or openings in the housing configured to receive sutures, staples, rivets or the like.

Stimulation treatments applied in embodiments disclosed herein may be monopolar or bipolar. However, in most applications, stimulation will be bipolar, with delivery and return electrodes built into the device. The distance between the electrodes in exemplary device 10A may be from a few mm up to several cm, with a typical spacing range of 1-5 cm. Electrode separation distances on the larger end of the range may require a bio-separable or composite device of the type described below in connection with FIG. 6 in order to enhance the safety and certainty of transmural migration and subsequent passage through the gastrointestinal tract.

Figure 1A:
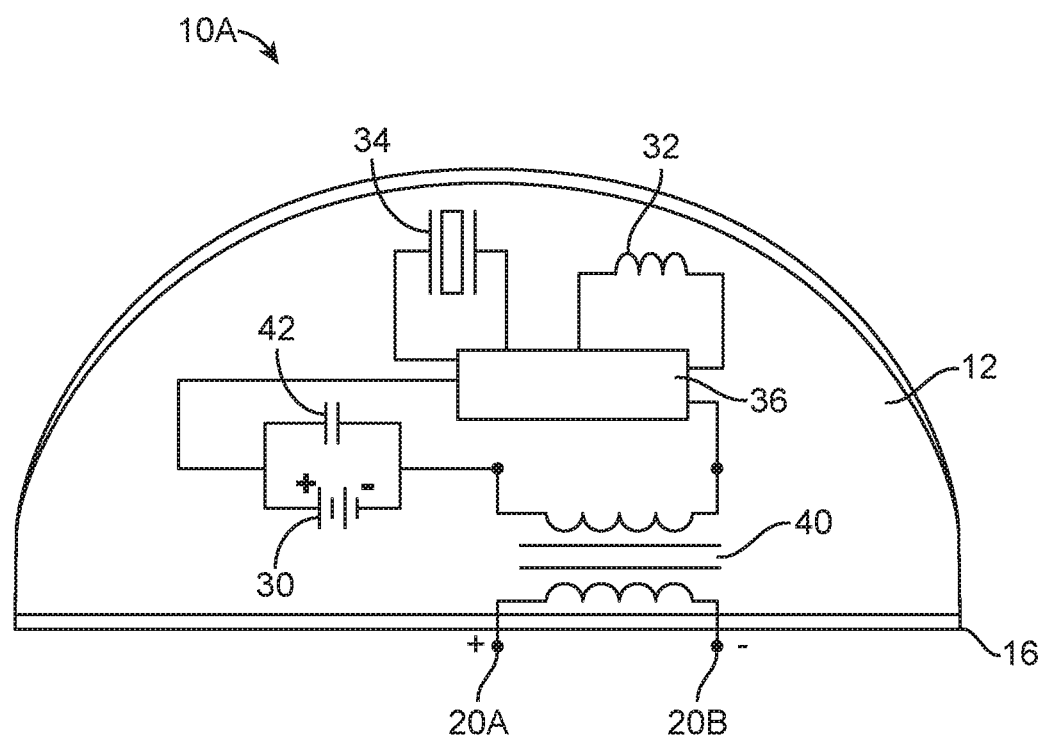
FIG. 1A schematically depicts components of an exemplary power and stimulation system applicable in disclosed devices.

Stimulation output and power supply may be devised for specific clinical indications by persons skilled in the art based on the teachings of the present disclosure. In one illustrative, exemplary configuration of device 10A, as shown in FIG. 1A, internal battery 30 cooperates with inductance coil 32 and piezoelectric element 34 to power the device. In this example, internal battery 30 may provide an initial charge, but also may be recharged via inductance coil 32, when a magnetic field is induced from outside the body to generate current therein, and/or by piezoelectric element 34, which when subjected to ultrasonic energy delivered from outside the body also generates electrical energy. Stored or generated electrical energy, controlled by control circuitry 36, which may include programmable logic and/or analog circuit elements, is delivered to electrodes 20A and 20B via optional transformer 40. Transformer 40 conditions the voltage applied through the electrodes as is well understood in the art. Depending on desired stimulation levels and power supply components, a separate transformer may or may not be included. As will be appreciated by persons of ordinary skill, other conventional circuit components required for safe operation of medical stimulation devices are well understood and thus will be understood to be included within control circuitry 36. In alternative embodiments, any of battery 30, inductance coil 32 or piezoelectric element 34 may be used alone or in any combination, along with other suitable power sources as may be determined by persons of ordinary skill. For example, when used alone, internal battery 30 may have a defined battery life, which in turn will define the treatment period. Such transcutaneous energy delivery methods are combinable not only with battery 30, but also may supply capacitor 42 to store the energy for longer, more consistent operation or higher-energy functions.

Figure 2:
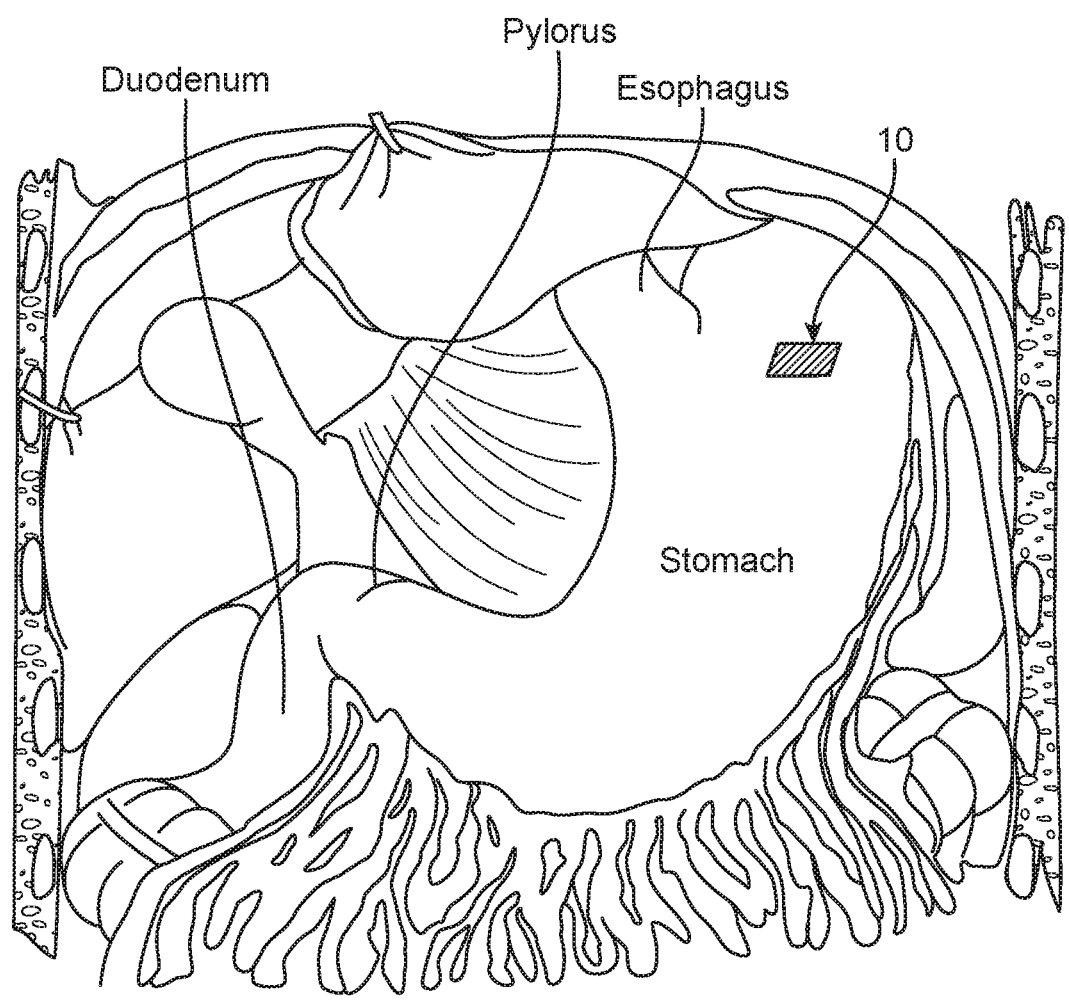
FIG. 2 schematically illustrates a device in accordance with embodiments disclosed herein disposed at a representative location on the greater curve of the stomach.

FIG. 2 illustrates exemplary device 10 placed at a representative location on the greater curve of the stomach. Note that device 10 represents a generic transmurally migratable device in accordance with the teachings of the present disclosure, which may comprise any of exemplary devices 10A-F as described herein or other variations based on the examples provided. Placement may be on the surface of the tissue with fixation as described above, or subsurface as explained below. A stimulation device positioned as shown in FIG. 2 may stimulate the stomach to alter gastric motility, create a feeling of satiety, and treat obesity. Stimulating in this location may also advance chyme into the proximal duodenum, which in a case of post-operative ileus, may stimulate peristalsis. As another example, a GI leak sensor (described below) placed as shown in FIG. 2 may be used to detect leaks or infection after bariatric surgery or gastric resection.

In certain clinical situations, it may be desirable to place device 10 partially or completely below the outer surface of the GI tract wall structure (sub-serosal). In such situations, a small slit or pocket may be created into which the device is partially or fully inserted, and then secured into place with an appropriate fixation means, for example by suturing the opening of the pocket closed over the device. Alternatively, the device may be attached to adjacent structures using bioresorbable materials, so that it is not initially affixed to the serosa directly. Determinations as to whether to use surface, sub-serosa or adjacent placement may be influenced by the desired duration of residence or speed of transmission of the device. These considerations are discussed further below.

As will be appreciated by persons of ordinary skill in the art, the size of stimulation and sensing devices 10 will depend in part on the size and shape of the specific stimulator or sensor to be implanted. In general, sizes for embodiments of device 10 may be about 2-15 mm in one or two larger dimensions (e.g., length, width or diameter) and about 1-3 mm in other dimensions (e.g., thickness). However, current stimulator and sensor technology allows miniaturization of most devices to the point where the operable stimulation or sensor components themselves are only a few millimeters across. Therefore, the shape and size of the overall device according to the teachings of the present disclosure may also be defined by the desired timing and process of transmural transmigration. For example, it may be desirable to make the overall device larger than dictated by its sensor or stimulation functionality so that the transmigration process takes longer. In some embodiments (see, e.g., device 10D, FIG. 5A), devices also may include perforations 17 through the device itself to allow areas for tissue ingrowth and to facilitate incorporation.

Figure 3:
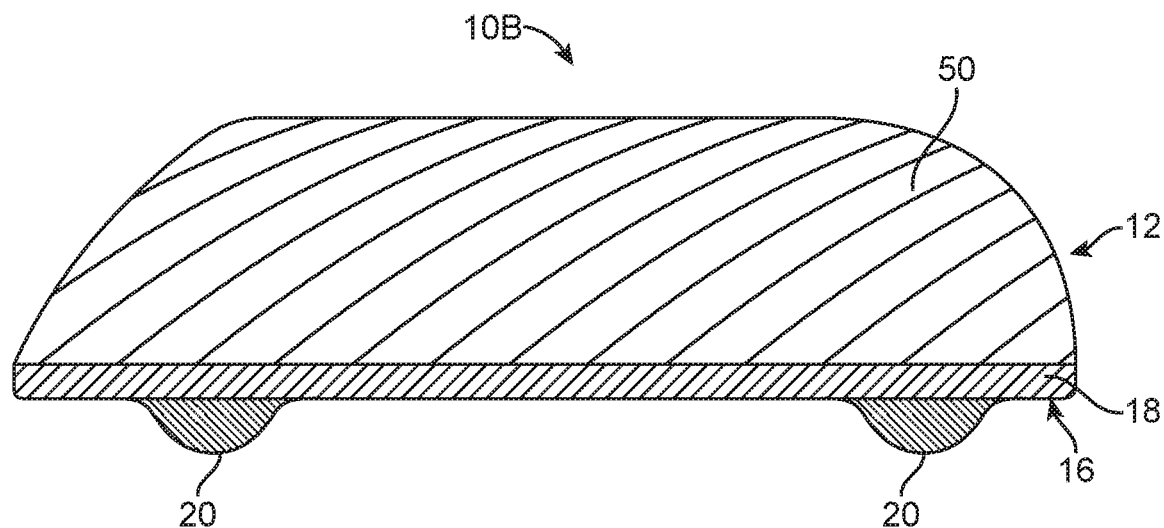
FIG. 3 schematically illustrates another exemplary embodiment of a stimulation device encapsulated in a coating or fabric to discourage tissue ingrowth.

In another exemplary embodiment shown in FIG. 3, device 10B is a stimulating device encapsulated in a tissue ingrowth discouraging coating or fabric layer 50. Layer 50 discourages ingrowth into the surface of the device in order to avoid undesired migration into tissue or organs that may lie adjacent to the target tissues and thus may come into contact with portions of the device. For instance, certain locations could cause the device to be positioned between the GI tract and the pancreas. In such locations, layer 50, serving as an anti-adhesion layer, would prevent unintended adhesion to the pancreas, while serosa-contacting side 16 would adhere the device to the serosa. Electrodes 20 protruding through or residing within gaps in adhesion-base layer 18 of serosa contacting side 16 allow treatment signals to pass through to target tissues. Materials or coatings suitable for anti-adhesion layer 50 may comprise a non-porous, non-expanded PTFE coatings, Parylene coatings, or even bioceramic coatings. Other aspects of device 10B may be substantially as described above with respect to device 10 or below with respect to further alternative embodiments of stimulation or sensor devices.

In addition to providing stimulation, electrical properties of disclosed devices may be configured to tailor the duration of residence. For example, the power supply (see, e.g., FIG. 1A) may be configured to electrically communicate with housing 12 or layer 14 to create a mild charge across one or more surfaces of the device in order to alter the biochemical micro-environment around the device. Mild charges may be used to alter local pH, influence the attraction or resistance of cells such as, in one example, fibroblasts involved in tissue healing. The surface charge effect thus can be used to create customized durations of residence. In these cases, as long as the device is powered and functioning it could repel incorporation and transmission. Once no longer wanted, the device is powered down, the repelling charge disappears, and incorporation into the serosa and transmission begins.

Figure 4:
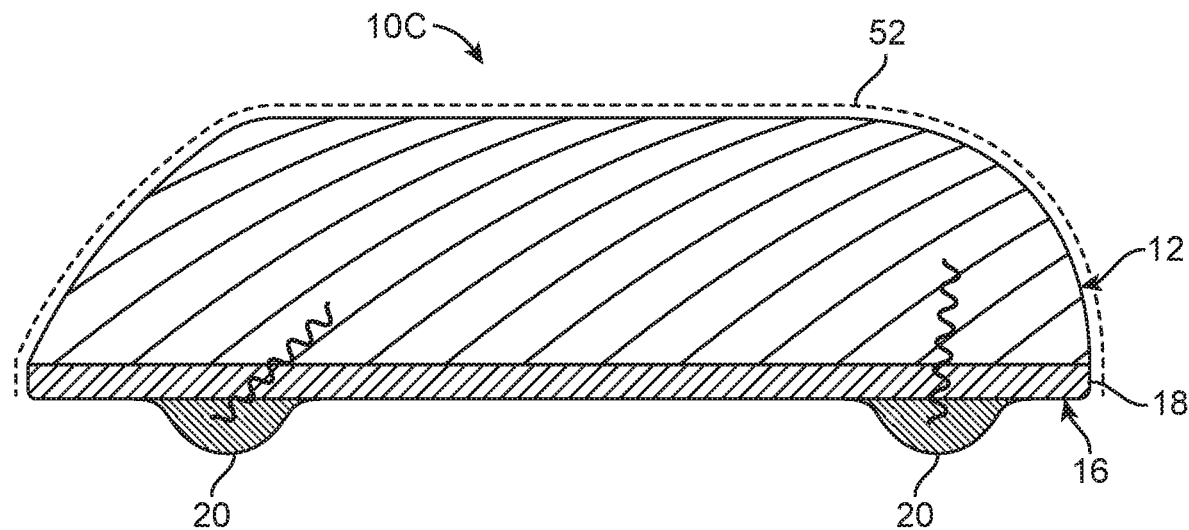
FIG. 4 schematically illustrates a further embodiment of a stimulation device having an electrically charged housing or outer surface.

FIG. 4 illustrates an embodiment of a device 10C utilizing the energy source of the device to impart a slightly charged outer layer at or around the encapsulation shell or housing 12 as described above. This charge can be adjusted to attract or repel cells as desired to encourage or discourage ingrowth, as previously described. The exemplary embodiment 10C in FIG. 4 is otherwise configured substantially as described above.

In addition to stimulation devices, as previously mentioned, a range of sensors providing clinically useful information may be configured in accordance with the teachings of the present disclosure for temporary placement on GI tract tissues or wall structures to permit transmural migration into the GI tract and natural expulsion from the body thereafter. For example, GI leak sensors, pH sensors, chemical and biological sensors, electrodes, accelerometers and pressure sensors could all be useful for monitoring a variety of conditions.

GI leak sensors are one example of a sensor type particularly well-suited to employ the teachings of the present disclosure. After surgical intervention, blood vessel or GI tract leaks can cause significant complications and infections. A sensor device configured as described herein to detect blood, bile or other materials via chemical sensors, stomach acid or the like via pH sensors, or infection and/or inflammation via temperature sensors may be affixed to or placed into contact with the wall of the GI tract. At a desired time after the peri-operative period has passed and the risk of leakage reduced or eliminated, the device migrates transmurally to the GI tract and passes. Illustrative examples of other sensor types include electrodes affixed to the digestive tract, and biological or chemical sensors within the peritoneum. For example, a series of electrodes affixed to the outside of the digestive tract may be used to monitor rate and strength of peristalsis. Other sensors may be configured to monitor chemical and other conditions in the peritoneum in patients undergoing peritoneal dialysis. Monitoring peritoneal fluid accumulation and composition in patients with ascites may be valuable in managing treatment. Biological or chemical sensors in the peritoneal cavity also may aid in the management of patients with gastrointestinal or abdominal cancers.

Figure 5A:
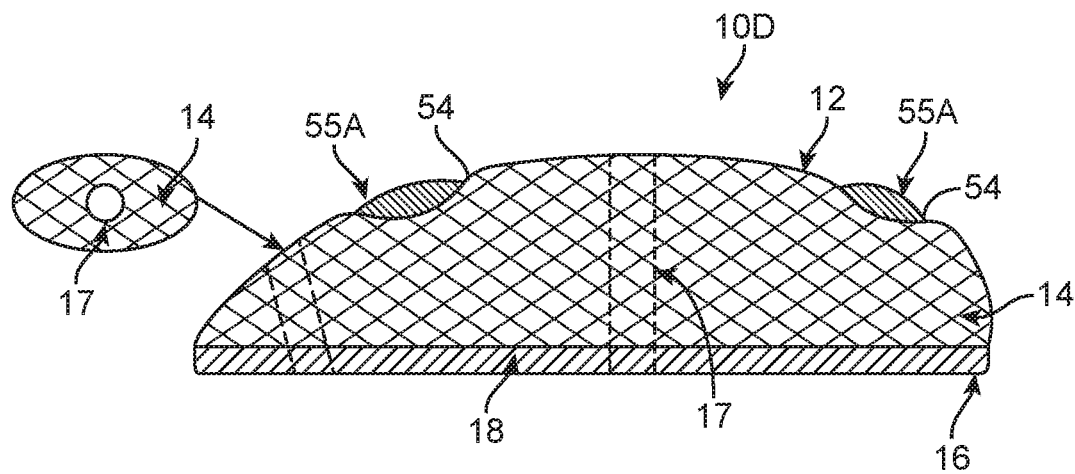
FIGS. 5A and 5B schematically illustrate exemplary embodiments of sensor devices.
Figure 5B:
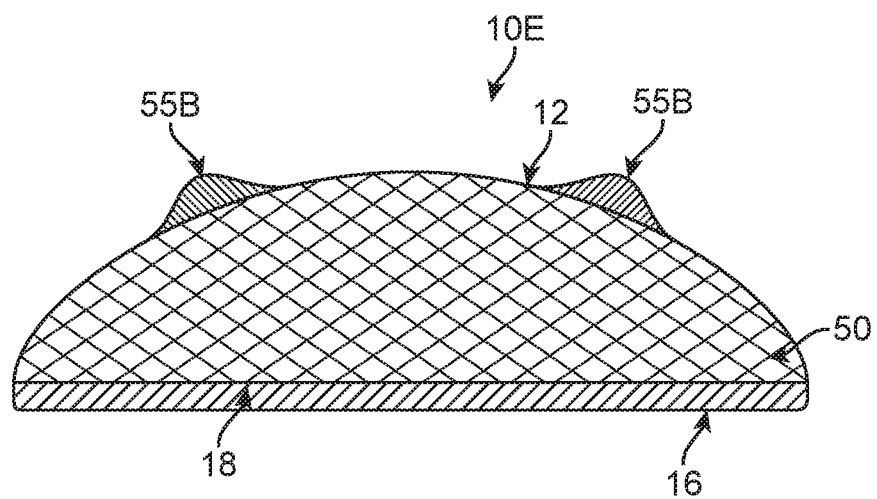

FIGS. 5A and 5B show exemplary embodiments of devices 10D and 10E, which may be configured to accomplish various sensor functions such as described above. In these configurations, coatings, coverings and surface treatments can be used as previously described, but the serosa-contacting stimulation electrodes are replaced with sensor elements residing within gaps in the coverings, protruding through the coverings, or over which the coverings have been modified to be rendered more permeable in the sensor regions. In general, passages into or through the device to facilitate fluid sampling may be provided, and coatings or coverings arranged, masked or perforated to appropriately accommodate the sampling requirements. For example, sensor device 10D has ingrowth encouraging covering 14 extending across housing 12, except where the housing defines perforations 17 to further encourage tissue ingrowth and at sensor ports 54 to expose sensor elements 55A to the surrounding environment. Alternatively, as shown in FIG. 5B, sensor device 10E is provided with anti-adhesion layer 50 surrounding housing 12, except where breaks in the anti-adhesion layer permit external sensor elements 55B to extend from the housing to communication with the surrounding environment. As a further alternative, or in combination with other surface layers, charged outer surface 52 may be employed (see FIG. 4). Other components of sensor devices 10D/E may be as described above. In other embodiments, sensor components of devices 10D/E may be combined with simulation components as in devices 10A-C to provide multi-functional transmurally migratable devices.

Figure 5C:
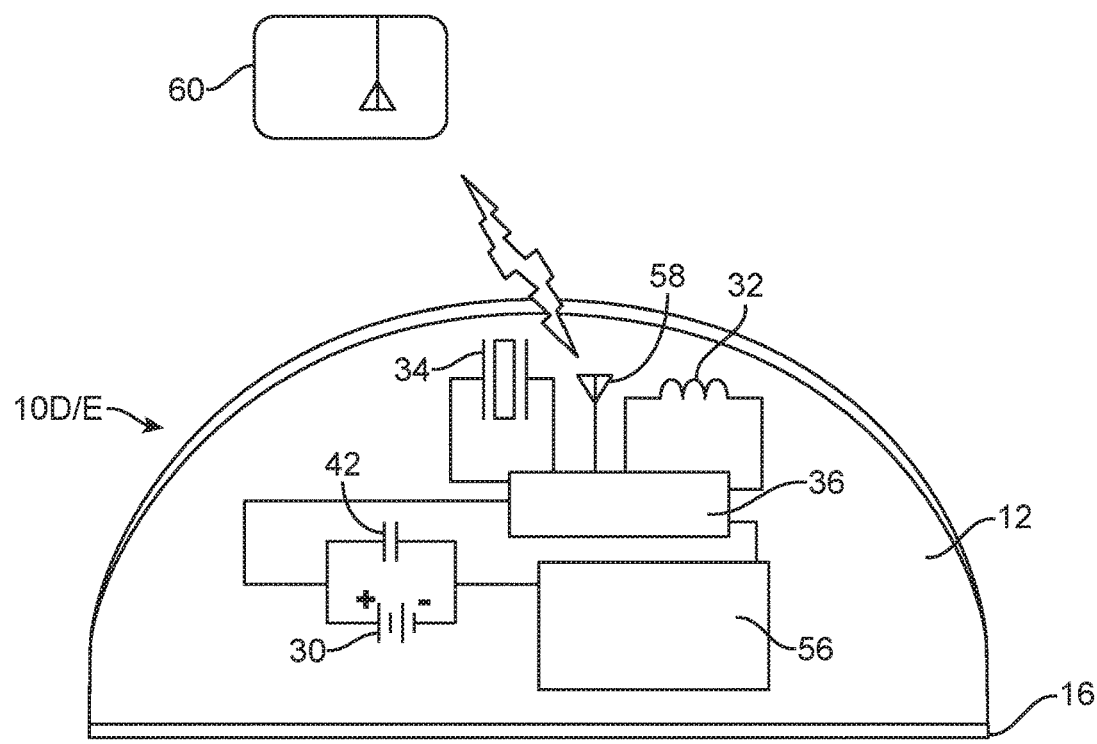
FIG. 5C schematically depicts components of an exemplary power and sensor/communication system applicable in disclosed devices.

One exemplary power, control and communication configuration for sensor embodiments 10D/E is schematically illustrated in FIG. 5C. Power supply and control may be substantially as in other embodiments described herein, shown, for example, in FIG. 1A. In order to convey sensed information to the healthcare provider, communications control module 56 is also provided. In an exemplary embodiment, sensor devices may communicate wirelessly with a receiver positioned outside the body, such as via antenna 58 communicating with external sensor 60. External sensor 60 may be positioned near sensor device 10D/E, for example on the abdomen of the patient immediately above the initial sensor device placement location. Appropriate hardware including circuitry and processors, as well as software implementing required communications protocols may be implemented by persons of ordinary skill in the art based on the teachings contained herein. In one exemplary communications protocol, sensor device 10D/E may be configured to transmit sensed information as long as the device is powered, or, alternatively, communications control module 56 may provide a receiving function to allow the healthcare provider to telemetrically control the device, such as turning the power on or off as desired, through external sensor 60 or another remote control device. Thus, in some embodiments, external sensor 60 may also function as an active controller rather than simply a passive sensor.

Embodiments disclosed above, while small or miniaturized, still contemplate unitary devices wherein minimum size may be dictated by required functional components. However, in some clinical situations, even that minimum size may present challenges. Thus, in some embodiments, depending on clinical situations presented, it may be desirable to have the device erode into two or more smaller pieces as the transmigration process begins or as part of that process. By providing for such device fragmentation, the creation of leakage paths through the GI tract wall may be avoided. Such leakage paths could arise if, at some point during migration, a unitary device becomes oriented to extend entirely through the GI wall so as to create a potential path from the inside to the outside of the GI tract. To avoid creation of a potential leakage path in this manner, in one exemplary embodiment, disclosed devices maybe configured to bio-erode into smaller pieces as transmural transmigration begins. The size of the bio-eroded pieces may be selected such that no single piece has a dimension large enough to extend transmurally through the tissue or wall structure into which it migrates. For certain indications, it may be advantageous to have a portion of the device migrate transmurally and be eliminated, while another portion of the device remains longer term or permanently within the abdomen. It may also be advantageous to have the outer surface of each piece coated or otherwise manufactured to promote tissue adherence to the piece, so that even if a piece did extend from inside the GI tract to outside of the serosa, there would be no leakage path along the surface of the piece.

Figure 6:
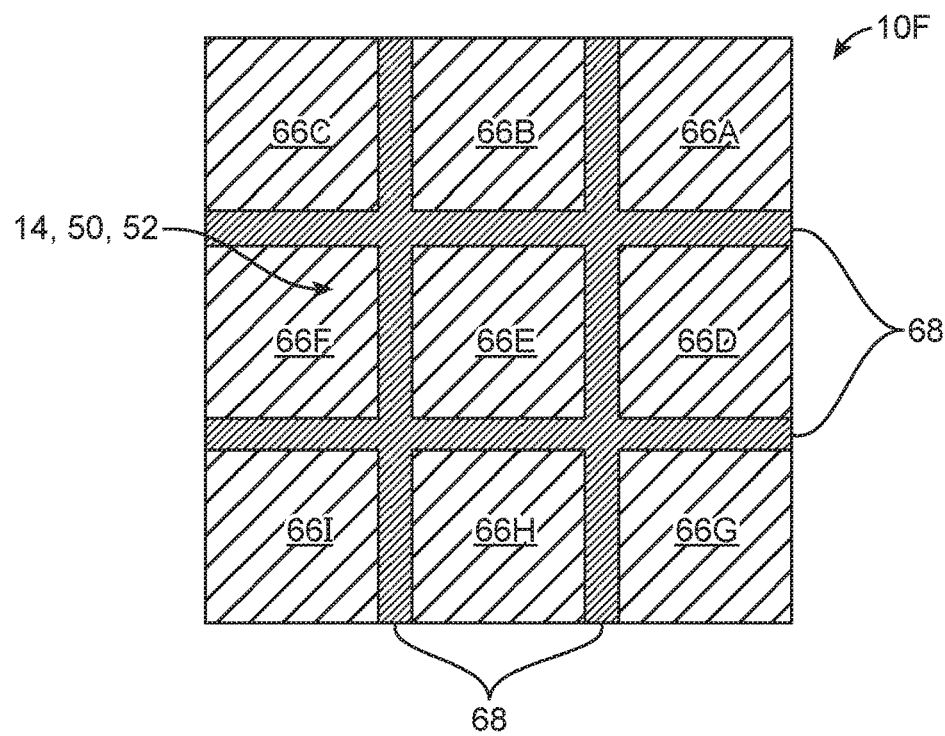
FIG. 6 schematically illustrates a top view of another exemplary embodiment comprised of plural sub-units.

FIG. 6 illustrates an exemplary configuration of a bio-erodible device 10F comprising sub-units 66A-I. Such a device may be a sensor or stimulator, or comprise sub-units providing multiple functionalities. Sub-units 66A-I are bound to one another by bio-erodible or electro-erodible binding component(s) 68 to create the larger operating unit. Binding components 68 may comprise materials such as polylactic acid (PLA) or poly-L-lactic (PLLA), or other materials used to create absorbable sutures and other bio-absorbable structures. After a period engineered into the material properties, typically a number of weeks, such materials soften and dissolve, allowing the sub-units to separate. Each sub-unit 66A-I individually, or device 10F as a whole, may be provided with any surface treatment or coating as described herein to promote or discourage tissue ingrowth, including any of layers 14, 50 or 52. As will be appreciated, any number of sub-units 66A-66(i) may be utilized. Also, in the FIG. 6 top view, serosa contacting side 16 is not visible.

Binding components 68 create sealed connections between sub-units 66A-I so that internal functional components, such as shown, for example in FIGS. 1A and 5C, may be distributed across the sub-units with appropriate electrical communication therebetween. In another example, functional components for sensor and/or stimulators may be disposed within individual sub-units, with power, control and/or communications provided centrally from a single sub-unit communicating through binding components 68 with other sub-units. Alternatively, device 10F may be a composite device in which sub-units 66A-I comprise individually complete functional units bound together to form an array of sensors and/or stimulators capable of covering a larger effective tissue area than any individual sub-unit device. In the example of composite devices, each sub-unit 66A-I may be formed as a separate device as described above and binding component 68 forms primarily a physical connection between the sub-unit devices. When device 10F is no longer required, based on time or externally provided signals, the device breaks down into its individual sub-units for easier transmigration through the wall of the GI tract.

Figure 7:
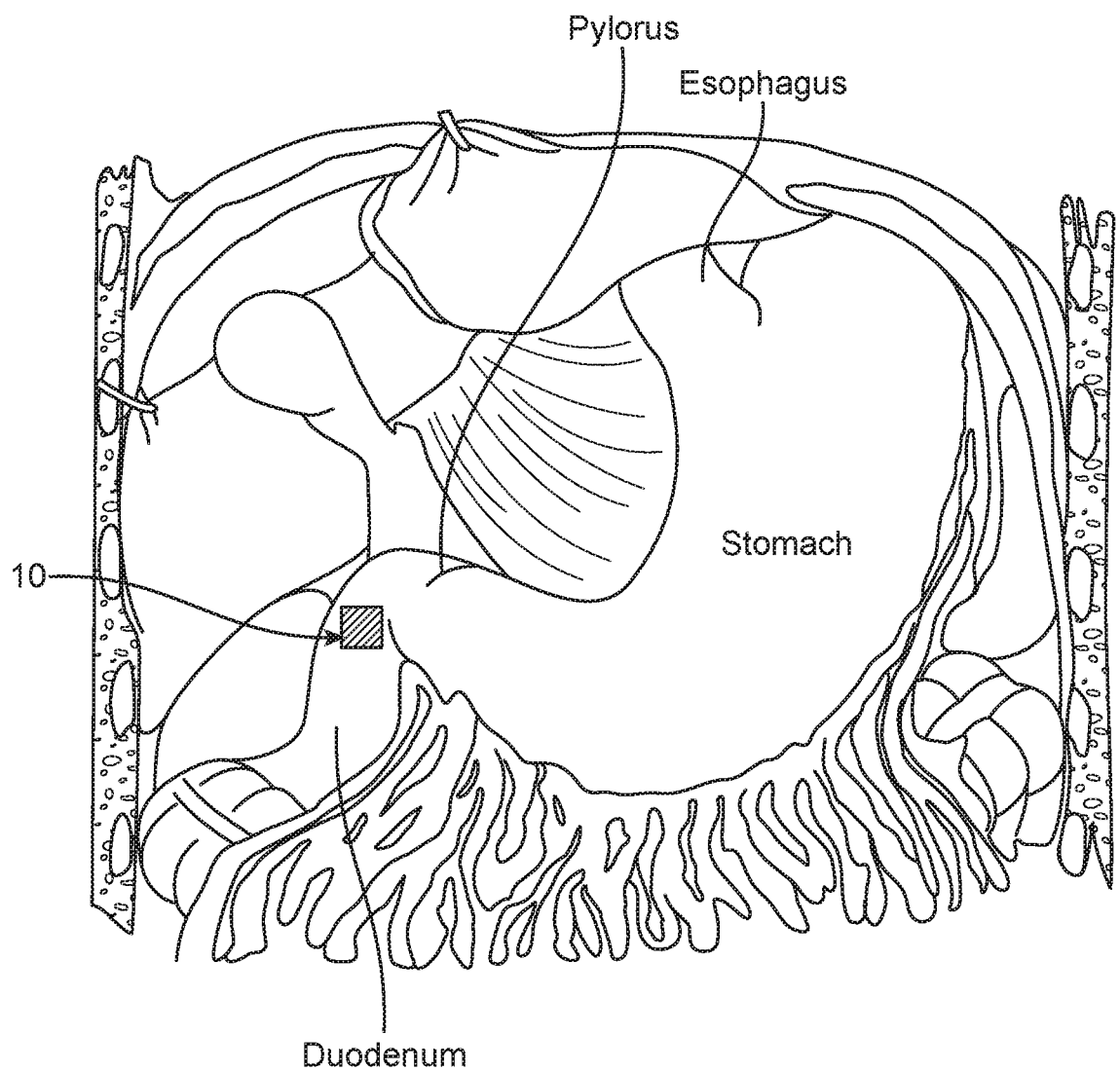
FIG. 7 schematically illustrates placement of an exemplary device to stimulate the duodenum and small bowel.
Figure 8:
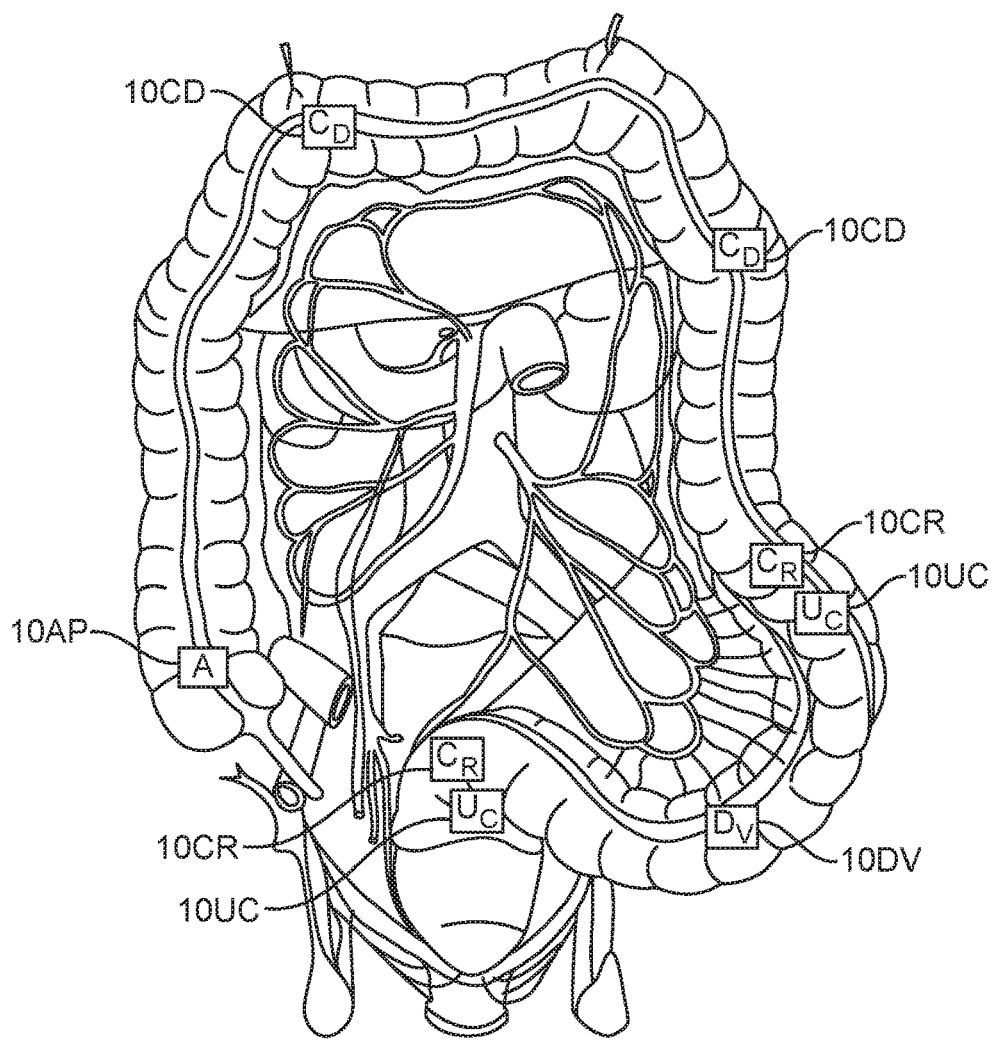
FIG. 8 schematically illustrates alternative placement locations for exemplary devices in the small and large intestine in accordance with embodiments disclosed herein.
Figure 9:
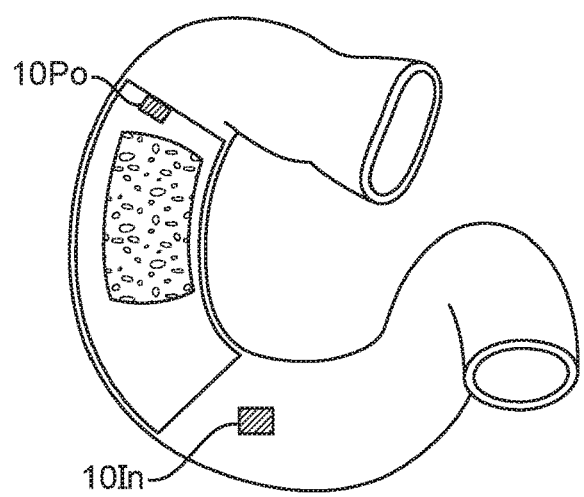
FIG. 9 schematically illustrates further alternative placements of exemplary devices on the serosa or in a subserosal area of a target organ.

As will be appreciated by persons of ordinary skill, transmurally migratable devices 10 as described herein may be usefully positioned in a variety of placement locations associated with the GI tract. One exemplary location on the greater curve of the stomach is illustrated in FIG. 2. Other exemplary placement locations are illustrated in FIGS. 7-9. For example, placement of stimulator device 10 at the location shown in FIG. 7 will stimulate the duodenum and small bowel to return to peristalsis in the case of post-operative ileus, and can facilitate enteral feeding in intensive care unit (ICU) patients. Alternatively or additionally, a sensor device 10 at the FIG. 7 location may be useful for detection of post-operative complications following proximal bowel resection, pyloroplasty, bariatric surgery or gastric resection.

FIG. 8 illustrates exemplary placement locations for sensor and/or stimulation devices 10 in the small and large intestine related to treatment or monitoring of various following conditions as indicated: AP=appendectomy; CD=Crohn's Disease; UC=ulcerative colitis; DV=diverticulitis; and CR=Colorectal cancer. The locations indicated in FIG. 8 are not intended to be specific or limiting, but are identified to demonstrate that devices according to the teachings of the present disclosure may also be placed in a variety of other locations in the small and large intestine to address a variety of conditions or indications.

FIG. 9 further illustrates exemplary placements of devices 10 on the serosa of a target organ (in this example the duodenum). Device 10 at location "Po" is illustrated as tucked partially or fully into a surgically created sub-serosal pocket. Device 10 at location "In" is illustrated as injected or inserted into the subserosal area using a needle or delivery device as schematically illustrated, for example in FIGS. 9A and 9B. In this manner, the device may be precisely placed on or between any layer of the wall structure of the GI tract.

Figure 9A:
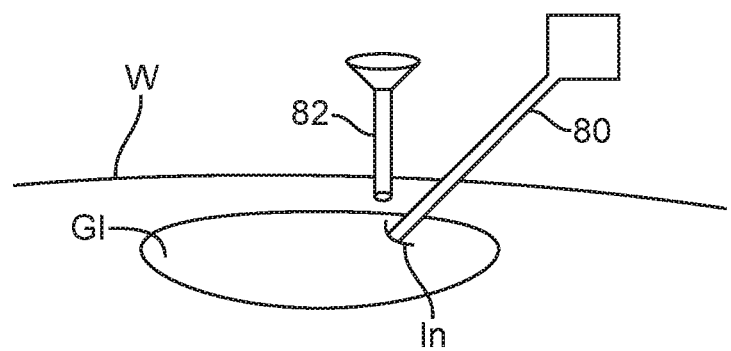
FIGS. 9A and 9B schematically illustrate delivery and a detail of a delivery device, respectively according to exemplary embodiments described herein.
Figure 9B:
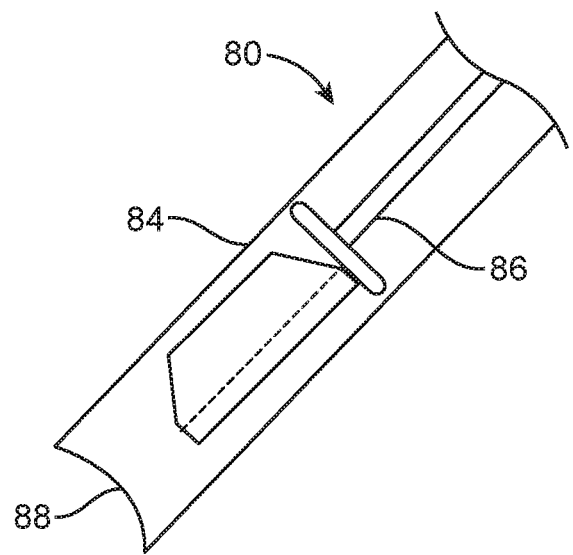

FIG. 9A shows delivery device 80 laparoscopically delivering device 10 (not shown) through the abdominal wall (W) to location "In" in a schematically depicted GI tract structure (GI). A separate laparoscope 82 may be used to visualize the insertion location. Exemplary delivery device 80, a distal end of which is illustrated in FIG. 9B, may comprise a delivery lumen 84 and advancement means 86, illustrated as a plunger in this embodiment, for advancing device 10 through lumen 84 and out of the device at the delivery location. Distal tip 88 may be sharpened to permit insertion directly into tissue without the need to separately form a pocket or other receiving tissue structure.

As previously mentioned, the amount of time that a device remains outside of the GI tract prior to completing transmural migration and excretion can be tailored by using different design considerations and materials. In general, total time for transmural migration through the GI tract wall structure may be about two months to two years, but once in the GI tract, devices will pass fairly quickly. For example, covering the device with woven surgical mesh material would ensure encapsulation of the device and transmission, and the weave of the material—density pattern and material—can be tailored to alter duration of residence. Woven Dacron polyester, woven ePTFE, and woven resorbable materials such as PLLA can all be adapted for this purpose. These materials which enhance encapsulation and tissue ingrowth will also minimize the risk of any leakage as the device migrates through the gastrointestinal wall.

Interspersing different materials for different purposes can further program the performance of the device. For example, biomedically adapted hook-and-loop-type fastening, self-adhesive material could be used as the serosal contact material, while the upper surface away from the serosa is partially or completely covered in an adhesion-barrier material such as low-internodal ePTFE in order to prevent adhesion to adjacent structures like the liver or pancreas and to slow transmission to provide longer duration times. Coatings can also be used to influence residence and transmission times. Parylene or other polymeric coatings or metallic coatings such as silver and titanium nitride can all be used for different applications as desired. Further, drugs may be incorporated into the device, coverings or coatings to provide anti-infective protection, or to influence the duration of residence/speed of transmission.

In another aspect of the present disclosure, it may be desirable in some embodiments to track the progress of the device transmurally and/or through the GI tract. For this purpose, various methods such as X-ray or ultrasound can be used to track the device and to determine whether it has passed. Alternatively, the device itself can provide tracking and telemetry. For example, a pH sensor on the device could detect that the device was within the GI tract. A signal can be emitted by the device that can be monitored externally to determine its presence. Optionally, an external system can be designed to interrogate the device so that the device is passive and the external monitor is active. Such tracking and telemetry may be readily accomplished by a person of ordinary skill via the communications module and external sensor as shown, for example, in FIG. 5C.

Embodiments described above utilizing transmural migration are well suited for placement on or within wall structures of the GI tract. However, in certain clinical situations, it may be desirable to provide treatment within the GI tract itself, while still providing that treatment with a temporarily implanted device. For example, in treating ileus, it may be desirable to deploy the treatment device through an NG or NJ tube directly to a location within the GI tract, either during surgery (in the case of patients undergoing abdominal surgery), or at any time for patients in the ICU.

Figure 10:
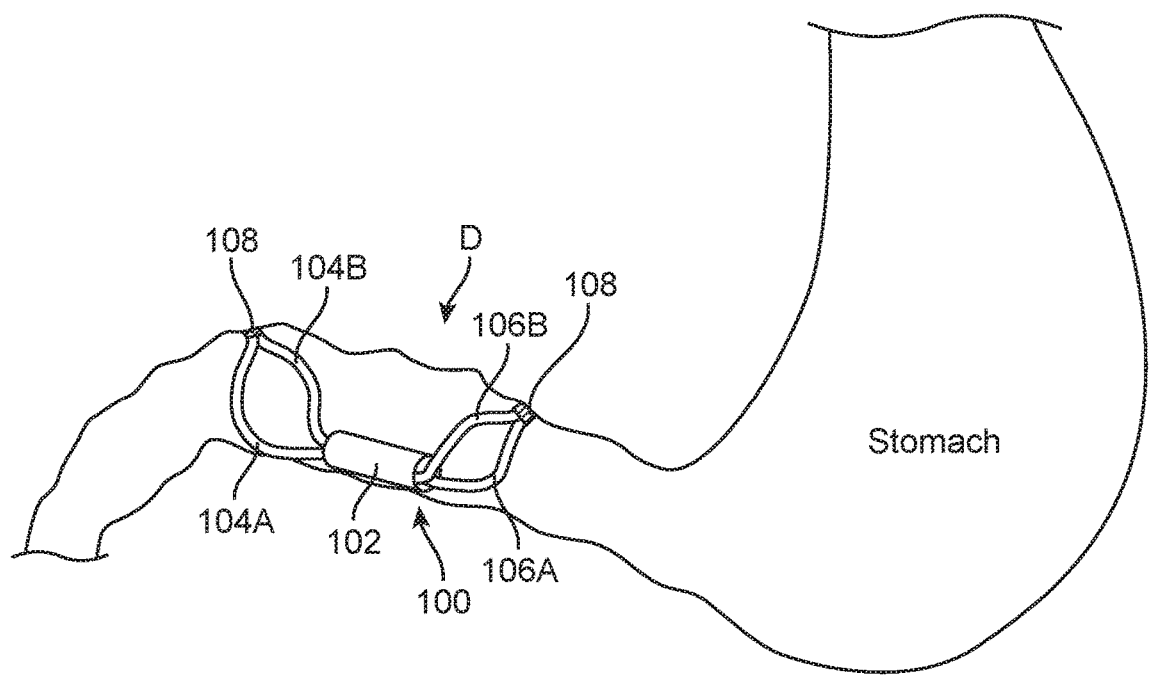
FIG. 10 schematically illustrates an embodiment of a temporary stimulator deployed in the proximal duodenum.

One exemplary embodiment of a temporarily implantable, NG/NJ tube deployable stimulation device 100 is shown in FIG. 10 deployed in the proximal duodenum (D). Exemplary device 100 may comprise body 102, with a pair of arms 104A,B and 106A,B disposed at each end. The body can contain any battery or power source, microelectronics, and other required electronic or sensor elements, and could be encased in a biocompatible metal or polymeric housing. The arm pairs may be manufactured from a resilient material or resilient composite structure and configured to form a circular shape upon deployment to hold device 100 firmly in place by contact with the GI tract inner wall surface. In this exemplary embodiment, electrodes 108 are disposed at the end of each pair of arms. Arms 104A,B and 106A,B may be made of a resorbable material, such as PLLA, PGLA, or another material which softens in a matter of days or weeks to allow the device to become dislodged and pass through the system. The arms (or coils described below) of resorbable material thus comprise other exemplary embodiments of bio-active fixation elements of the present disclosure. Thin, flexible wires connecting the electrodes to internal power supply and control components are embedded within the arms and thus not visible in the figure.

Device 100 may need to remain in place through several hours or days of gastrointestinal peristalsis, and through several meals eaten by the patient. So the design must resist peristalsis for a period of time, and then soften to the point where it advances predictably and safely through the gastrointestinal tract under peristalsis. The overall shape of device 100, including body 102 and the arm pairs is configured so that it is positioned and firmly held in place with the stimulating electrodes firmly against the wall of the gastrointestinal tract, and in alignment with the gastrointestinal tract. This can be accomplished by shaping the device so that the body and arms all lay against the walls of the intestine, rather than in the middle where it may be more easily dislodged by passing food. It can also have a surface which is very rough or textured to grip the surface of the GI tract, resisting migration during peristalsis until this surface has eroded. If the device were positioned backwards, it might lead to retrograde stimulation which impedes rather than encourages forward peristalsis.

Device 100 as a whole also has a size, shape and flexibility that allows it to be advanced through a typical NG or NJ tube, and also to advance through the gastrointestinal system after the desired period of stimulation is completed. This means, generally, a diameter of 3-5 mm if intended to be deployed through all size tubes without requiring the healthcare provider to select a larger size tube than might otherwise be selected for the patient. In some embodiments, the diameter will be preferably about 4 mm or less. The flexibility requirement generally will require a rigid length of no more than about 15-20 mm. However, overall length must be sufficient to provide a spacing of the stimulation electrodes of 20 mm or more for best stimulation results in the GI tract. Thus, exemplary embodiments, which may be stretched out to as much as about 15 cm for deployment through the delivery tube may be only about 2-6 cm in length after deployed and expanded to fix against the GI tract wall.

Device 100 may be powered, controlled, deliver stimulation and communicate in substantially the same manner as devices 10. The arrangement of power, control and stimulation components thus may be substantially as described above in connection with FIGS. 1A and 5C; however, packaged according to the size and shape requirements of device 100 and related tube-deliverable embodiments hereinafter described. However, one variation from previously described embodiments may be in the size of the inductance coil if power or charging is accomplished via a transcutaneous inductive power system. As is known in the art, the larger the diameter of the inductance coil, the greater the power that can be delivered. In this regard, the design of an inductive power system for a tube delivered device such as device 100 may take advantage of device positioning within a relatively large lumen like structure by employing one or more coils which expand to approximately the diameter of the intestinal tract, but which can be compressed to a small diameter for delivery. In some instances, the combination of such a coil, plus a simple capacitor, may be a less expensive and/or safer power source than a battery.

Figure 11:
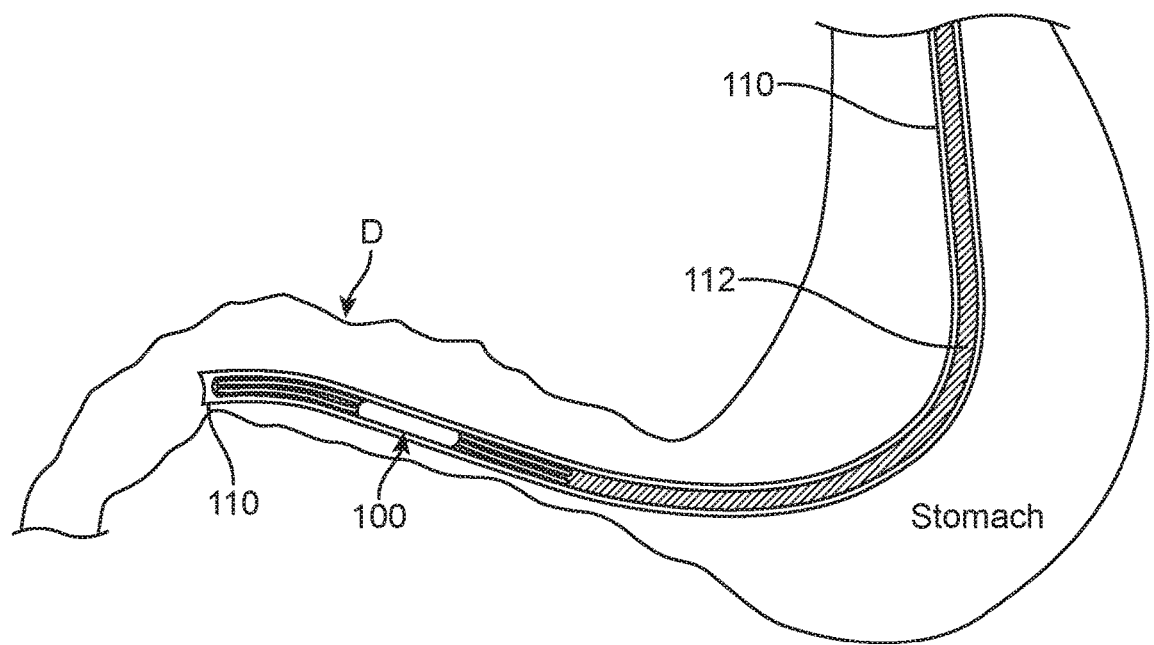
FIG. 11 schematically illustrates an embodiment of a temporary implantable stimulator being deployed through a nasogastric/nasojejunal (NG/NJ) tube.

FIG. 11 shows exemplary device 100 being advanced for deployment through NG/NJ tube 110. NG/NJ tube 110 may comprise an ultra-thin wall tube, for example manufactured with a polymer reinforced with metallic braid or a coil to maximize space available for delivery of device 100, while still maintaining an average outside diameter in the typical range of about 6 mm and minimizing the risk of kinking. In this exemplary embodiment, device 100 is releasably attached to stylet 112, which advances the device through tube 110 to the desired deployment location. Alternatively, delivery tube 110 may be placed at the deployment location and device 100 deployed by holding stylet 112 in a fixed location and withdrawing the NG/NJ tube to release the device. In a further alternative, device 100 may be deployed by advancing it hydraulically by injecting fluid such as saline under pressure behind the device in the delivery tube.

A temporary intraluminal electrical stimulator for the gastrointestinal system, such as device 100, which can be placed in the stomach or small intestine through an NG or NJ tube as described herein allows the device to be delivered during surgery in any patient undergoing abdominal surgery who may be expected to be at moderate or high risk for ileus. During the surgery, when an NG or NJ drainage tube is in place, the device can be inserted through the tube, which would already be in place as a routine part of such surgery. The surgeon can confirm the appropriate location of the tube by palpating the stomach and duodenum to feel the presence of the tube, obviating the need for an endoscope to confirm its location. This is often done now in both open and laparoscopic surgeries.

Figure 12:
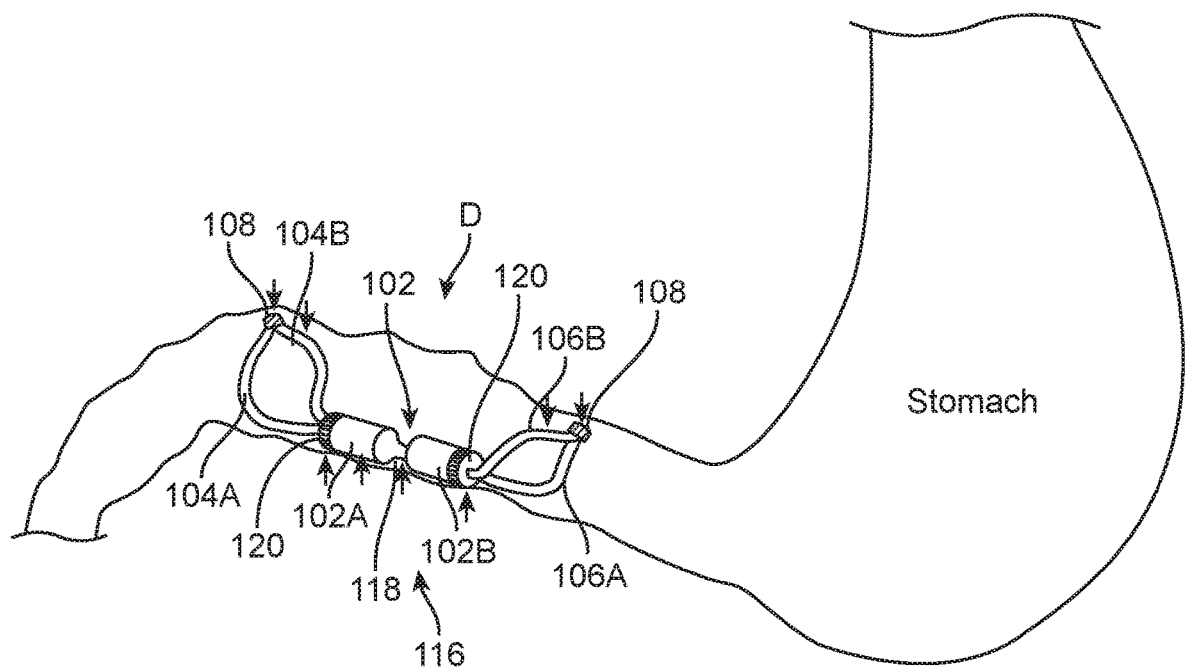
FIG. 12 schematically illustrates an embodiment of a temporary implantable sensor having two body sections separated by a flexible section.

To meet the potentially conflicting flexibility and length requirements for a tube deliverable device as explained above, the main body of the device may be provided with one or more flexible joints along its length. One such exemplary embedment is shown in FIG. 12, wherein stimulator device 116 includes body 102 with two sections 102A and 102B, joined by flexible section 118. This configuration allows body 102 to flex as device 116 is delivered and as the device passes through the rest of the gastrointestinal tract. Arms pairs 104A,B and 106A,B and electrodes 108 may be configured substantially as described above. Alternatively, or additionally, electrodes 120 may be provided at each end of the body 102. The flexible, segmented structure of sections 102A and 102B, joined by flexible section 118, may permit electrodes to be positioned a sufficient distance apart on the body itself.

Figure 13:
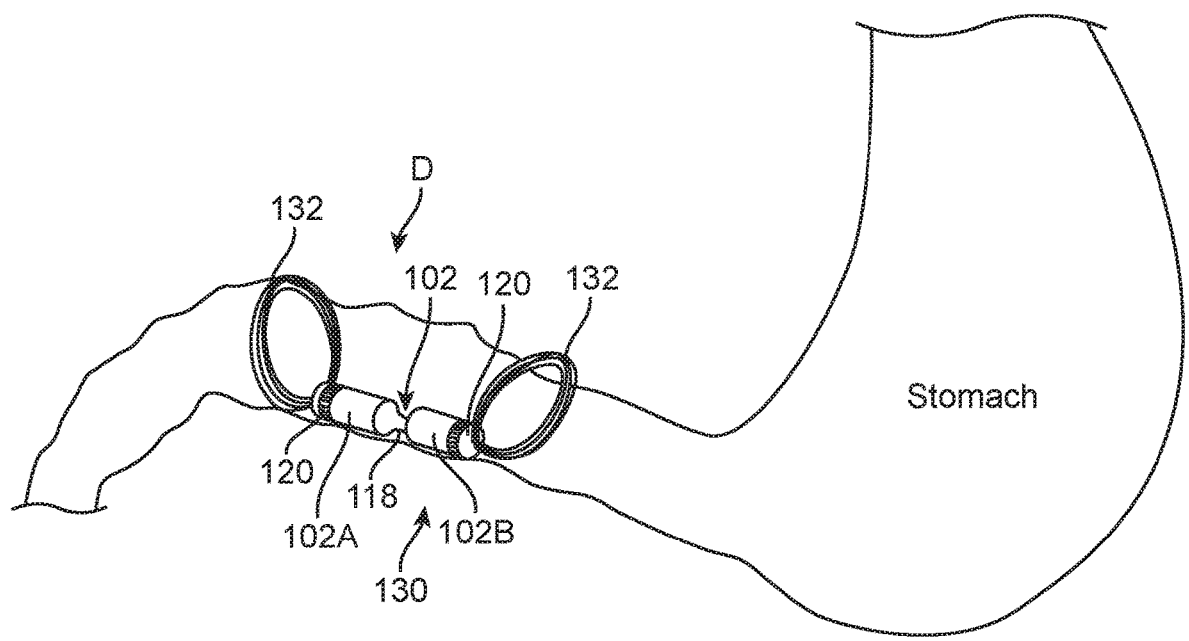
FIG. 13 schematically illustrates a further embodiment of a temporary implantable stimulator having dual-purpose end coils.

In another alternative embodiment, device 130, shown in FIG. 13, is a stimulator with coils 132 at each end of body 102. Coils 132 also comprise a resorbable or softenable material with embedded thin flexible wires to both hold device 130 in place, by engaging the organ or lumen wall where placed, and serve as inductance coils (see 32, FIGS. 1A and 5C) to provide power to the device from an externally generated magnetic field. Coils 132 also may be configured to serve as antenna for communication with a controller outside the body (see 58, 60, FIG. 5C). In the embodiment illustrated, electrodes 120 are positioned at the end of each body segment 102A and 102B. Alternatively, coils such as coils 132 also may be configured to be contained within the arm pairs of devices 100 and 116 shown in FIGS. 10 and 12.

Figure 14:
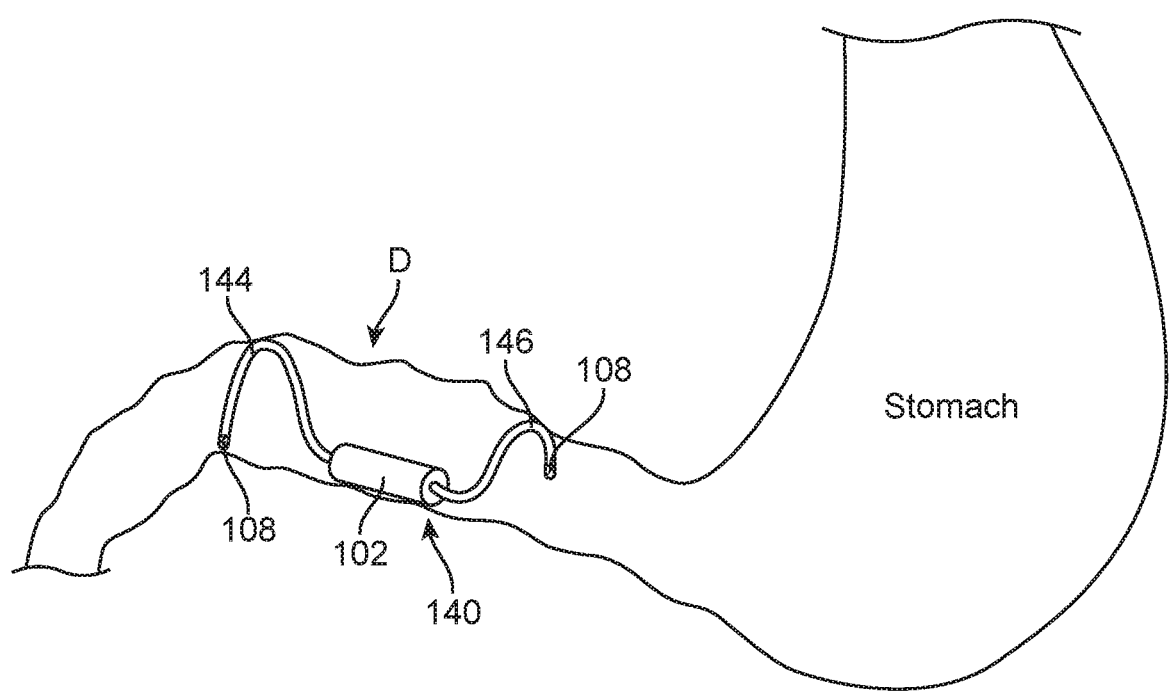
FIG. 14 schematically illustrates yet another embodiment of a temporary implantable stimulator with end coil arms.

In a further alternative as shown in FIG. 14, stimulation device 140 includes arms 144, 146 at each end configured in a coil shape. Electrodes 108 are positioned at the end of arms 144 146, or may be provided on body 102 where sufficient body length is provided to achieve desired electrode spacing. Device 140 may be otherwise configured as described above, whether with a unitary or segmented body 102.

Operation of stimulation devices 100, 116, 130 and 140 may be accomplished in a generally conventional manner, that is by communication with outside controllers to turn the device on or off, and to adjust stimulation treatment parameters such as rate, amplitude, or pulse duration. Persons of ordinary skill in the art will be well versed in this type of control. However, such a conventional control approach requires a healthcare provider to actively turn on the device at the appropriate time point, for instance 24 hours post-surgery, and thereafter set treatment parameters as needed.

Further aspects of the present disclosure provide alternative control methodologies wherein device operation may be automatically initiated by the implantation of the device. In one exemplary embodiment, immersion of the device in the fluid within the gastrointestinal tract completes a circuit between two contacts which turns on an electronic timing circuit. In another embodiment, a mechanical spring switch is held open by a material which dissolves at a predictable rate in gastrointestinal fluids. This material could be any one of a number of materials which are generally regarded as safe, such as gelatins used to make capsules for pills taken orally, or various starches or sugars which could be optimized to dissolve at a predictable rate regardless of the acidity of the gastrointestinal fluids. A further exemplary embodiment may initiate the time-delayed starting process at the time of implantation by the physician by activating a sealed, external switch on the device or by use of an independent controller communicating with the device as previously described.

Similarly, the device may be turned off by remote radio control device, or automatically after a certain period of activity. Automatic shut-off may be controlled by a timing circuit within the device, or by configuring the power supply, such as a battery, to be exhausted after a desired treatment interval. While this could mean that the stimulator is providing a signal for somewhat longer than is absolutely necessary, the additional stimulation may not be harmful to the gastrointestinal system's function, and it further simplifies the management of these patients, obviating the need for active sensing and management of the patient's gastrointestinal status.

Based on the teachings herein contained, persons of ordinary skill in the art will appreciate that disclosed embodiments provide stimulation devices that can be placed into the gastrointestinal tract to provide stimulation for a few hours, days, or weeks to treat ileus, without any attached wires or catheters running through the nose or mouth. After providing stimulation for some days or weeks, the disclosed devices then pass naturally through the gastrointestinal tract and are excreted. Disclosed embodiments thus avoid the need for a prolonged presence of an NG/NJ tube. In conjunction with the disclosed devices, a new NG/NJ tube with ultra-thin walls may be employed, to enable the delivery of this device into the desired location in the gastrointestinal tract while keeping the overall outside diameter of the NG/NJ tube at approximately 6 mm, which is common for surgical NG drainage tubes.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:
1. A temporary implantable GI device, comprising:
   housing securable to a tissue structure of the GI tract;
   interface elements disposed with the housing to monitor or stimulate the GI tract through said housing;
   functional elements within the housing configured to provide power and control for the interface elements; and one or more bio-active fixation elements configured to secure the housing at a selected treatment location on or in the GI tract structure and to release the housing into the GI tract after a determined time so as to be passed from the body through natural processes of the GI tract after said release, at least one said bio-active fixation element comprising a tissue ingrowth promoting layer configured to permit transmural migration of the device through the tissue structure into the GI tract disposed at a surface of said housing.

2. The device of claim 1, wherein:
said one or more bio-active fixation elements comprise at least first and second elements each comprising at least a part of an outer surface of the housing;
said first element comprises a material configured for tissue ingrowth to permit transmural migration of the device through the tissue structure into the GI tract forming said tissue ingrowth promoting layer; and
said second element comprises a material configured for adhesion to a GI tract tissue structure for initial device placement.

3. The device of claim 1, wherein said one or more bio-active fixation elements comprise expandable bio-resorbable arms configured and dimensioned to securely engage an inner wall of the GI tract when expanded therein.

4. The device of claim 1, wherein:
said interface elements comprise at least one sensor element; and
said functional elements comprise a sensor control module communicating with said at least one sensor element.

5. The device of claim 1, wherein:
said interface elements comprise at least one electrode adapted to contact adjacent tissue; and
said functional elements comprise a stimulation control module communicating with said at least one electrode.

6. The device of claim 1, wherein
said tissue ingrowth promoting layer comprises at least one of a surface treatment or coating comprising an expanded polytetrafluoroethylene (ePTFE) adhered to said surface, or an open weave fabric around said surface.

7. The device of claim 6, wherein said ePTFE has an inter nodal distance (IND) of approximately 80-120μ.

8. The device of claim 6, wherein said second bio-active fixation element comprises a material configured to promote adhesion to the serosa.

9. The device of claim 1, wherein said first bio-active fixation element comprises an electrically charged surface on said housing.

10. A method of diagnosis or treatment in the GI tract by temporary implantation and non-invasive removal of a diagnostic or treatment device, said method consisting essentially of:

securing the device at a selected location on an outside of GI tract tissue with a bio-active fixation element specifically configured to release the device into the GI tract after a determined time so as to be passed from the body through natural processes of the GI tract after said release, said bioactive fixation element comprising an outer tissue ingrowth promoting layer;
the device transmurally migrating through the GI tract tissue before said predetermined time at least in part due to the interaction of the outer tissue ingrowth promoting layer with the GI tract tissue; and
operating the device before the end of the determined time.

11. The method of claim 10, wherein the selected location is specifically selected to ensure that the device resides fully within the GI tract after release by the bio-active fixation element.

12. A temporary GI treatment or monitoring device allowing non-invasive removal, comprising:
a sealed housing of bio inert material;
a bio-active layer tissue ingrowth promoting layer disposed at a surface of said housing, said bio-active layer specifically configured to promote transmural migration of the device through GI tract tissue;
fixation means on the housing;
at least one interface element configured to provide treatment or to monitor and to extend through or beyond the housing; and
control and power supply components disposed in the housing communicating with the at least one interface element.

13. The device of claim 12, wherein the at least one interface element comprises at least one stimulation electrode.

14. The device of claim 12, wherein the at least one interface element comprises at least one sensor element.

15. The device of claim 12, wherein said tissue ingrowth promoting layer comprises at least one of surface treatment, coating adhered to said surface, or fabric around said surface.

16. The device of claim 15, wherein said fabric comprises an open weave fabric.

17. The device of claim 15 wherein said surface treatment or coating comprises an expanded polytetrafluoroethylene (ePTFE).

18. The device of claim 17, wherein said ePTFE has an inter nodal distance (IND) of approximately 80-120μ.

19. The device of claim 12, further comprising a second bio-active layer on a portion of the housing, wherein the second bio active layer comprises a material configured to promote adhesion to the serosa.

* * * * *